United States Patent [19]

Stevens

[11] Patent Number: 5,419,340

[45] Date of Patent: May 30, 1995

[54] GUIDABLE CATHETER ASSEMBLY USING COATED DEFLECTOR WIRE AND METHOD OF USING SAME

[76] Inventor: Robert C. Stevens, 18265 NW. Highway 335, Williston, Fla. 32696

[21] Appl. No.: 144,202

[22] Filed: Oct. 27, 1993

[51] Int. Cl.⁶ .................................... A61M 25/00
[52] U.S. Cl. .................................... 128/772; 128/657
[58] Field of Search ............... 128/657, 772; 604/93, 604/95, 164, 176, 280, 282

[56] References Cited

U.S. PATENT DOCUMENTS

| | | | |
|---|---|---|---|
| 3,503,385 | 3/1970 | Stevens | 128/657 |
| 3,922,378 | 11/1975 | Kline | 128/772 X |
| 4,003,369 | 1/1977 | Heilman et al. | 128/772 |
| 4,080,706 | 3/1978 | Heilman et al. | 128/772 X |
| 4,548,206 | 10/1985 | Osborne | 128/772 |
| 4,579,127 | 4/1986 | Haacke | 128/772 |
| 4,811,743 | 3/1989 | Stevens | 128/772 |
| 4,884,579 | 12/1989 | Engelson | 128/772 |

*Primary Examiner*—Sam Rimell
*Attorney, Agent, or Firm*—Fay, Sharpe, Beall, Fagan, Minnich & McKee

[57] ABSTRACT

A specialized control wire for use in the guidance of catheters includes a stainless steel core wire having a ball formed on the distal tip of the wire. The control wire is resiliently biased into a linear orientation for the purposes of selectively deflecting the curved distal portion of a catheter into relaxed and unrelaxed positions. The control wire is covered at least in part with a low friction material. One such low friction material is polytetrafluoroethylene (PTFE) commonly available as Teflon ® (a registered trademark of e.i. DuPont). Other lubricating materials may also be used such as hydromers and some silicones.

22 Claims, 3 Drawing Sheets

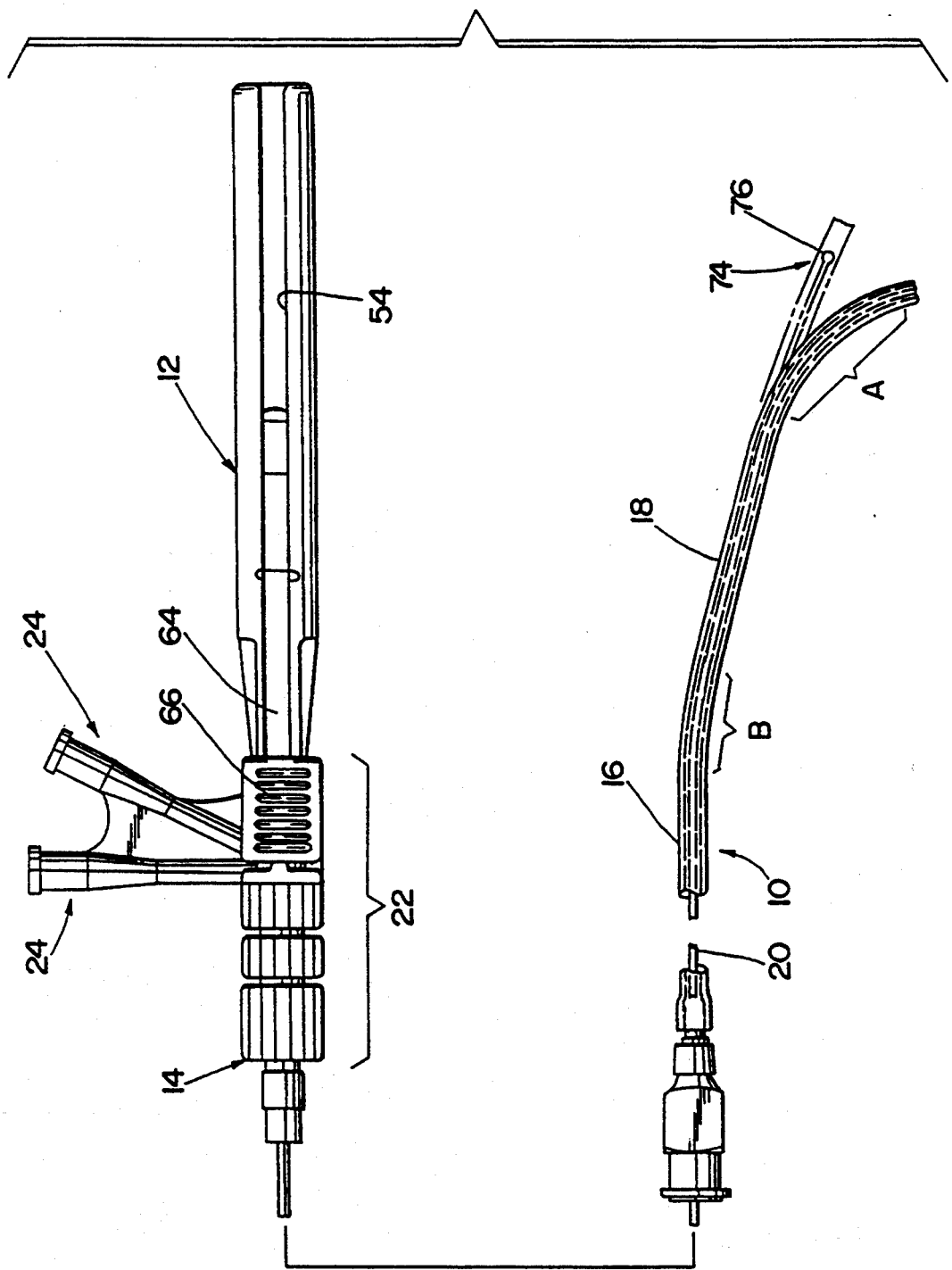

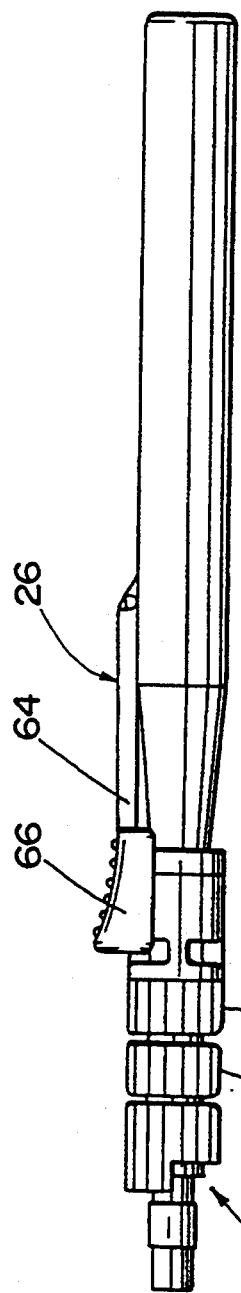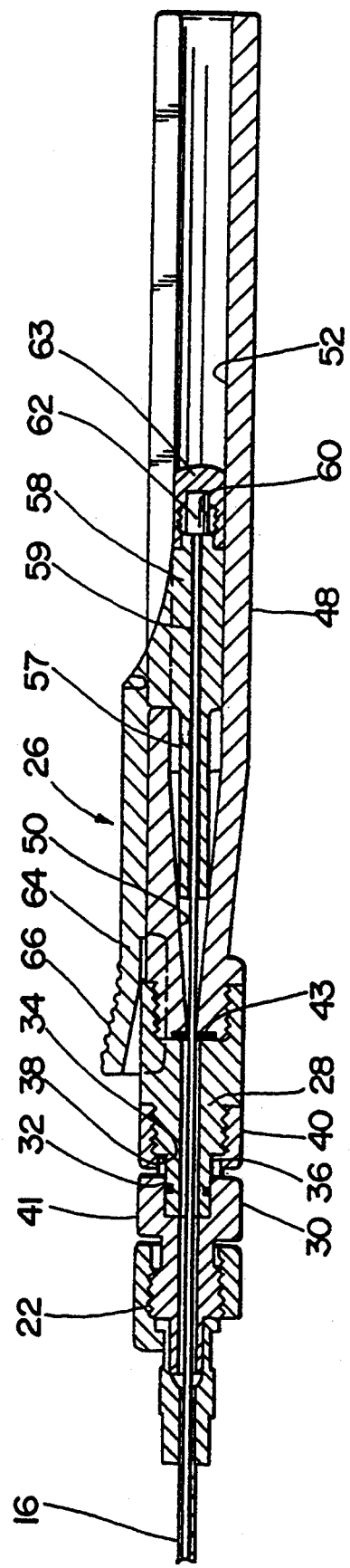

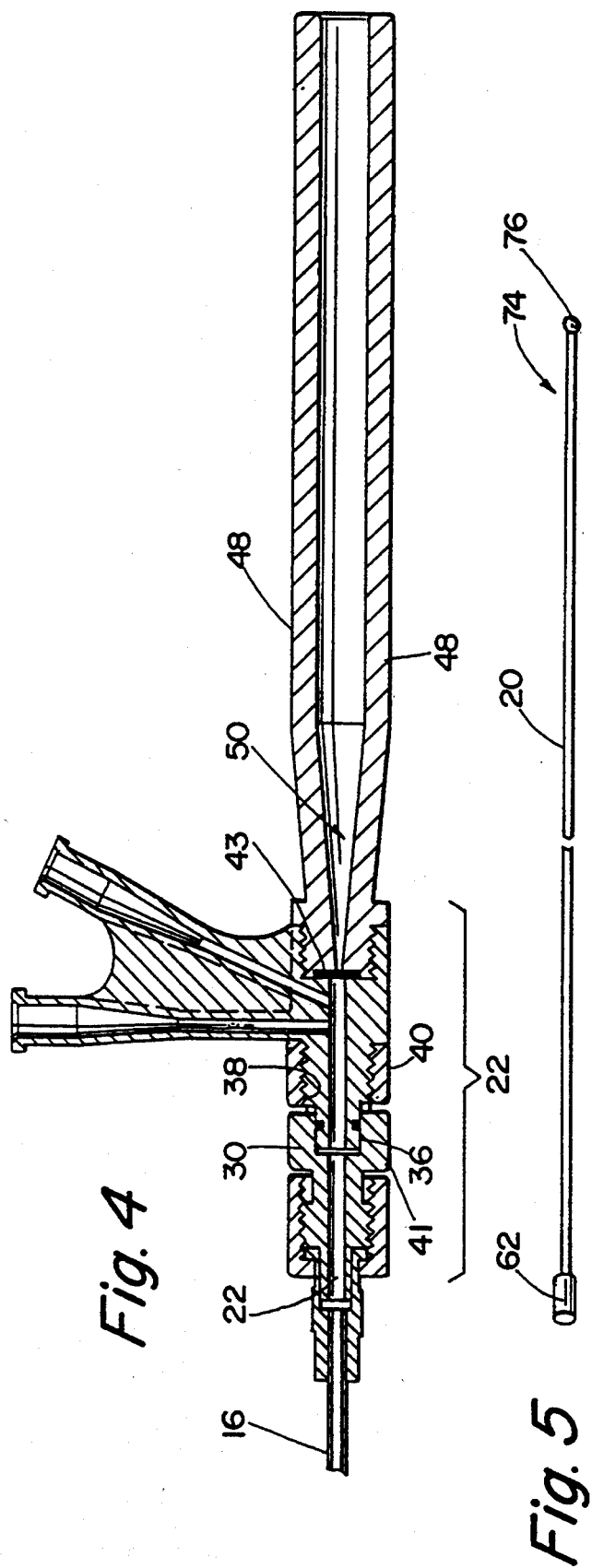
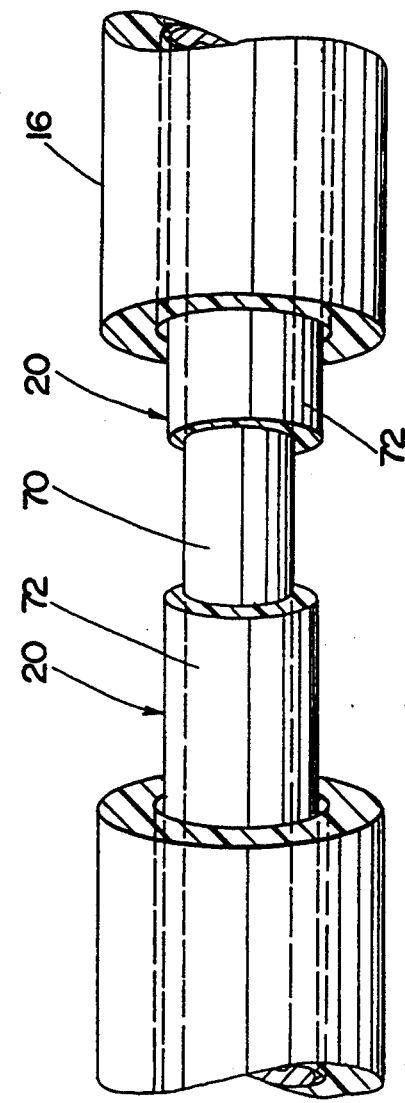
Fig. 4
Fig. 5
Fig. 6

GUIDABLE CATHETER ASSEMBLY USING COATED DEFLECTOR WIRE AND METHOD OF USING SAME

BACKGROUND OF THE INVENTION

The subject invention is directed to the art of vascular catheters and, in particular, to the guidance of catheters using a low friction resilient control wire during introduction of catheters in such techniques as angiography and arteriography.

In certain diagnostic techniques, it is necessary to insert a catheter through the blood vessels to a particular destination, and this frequently makes it necessary to guide the catheter into one of several alternate channels, as into a branching vessel. Vascular catheters have heretofore been commonly formed with a curved but flexible distal tip portion which may be used to guide the cannula by twisting it from side to side during insertion to select the desired one of several vessels. Attempts have been made to control the curvature of the distal tip alone so that it may be directed forward or to the side as desired during its insertion. This technique has meet with little success.

Another prior art guidable catheter mechanism includes a flexible catheter body tube which is formed to be as rigid in torsion as possible, while being longitudinally flexible, so that the entire body of the catheter may be twisted from side to side even though it be in a circuitous or tortuous path, and without a tendency to whiplash, that is to resist turning until a certain torque is applied at which time the entire rotation applied to the proximal end is unleashed. One such system is described in my U.S. Pat. No. 3,503,385.

In this earlier patent named above, forward guidance is provided by forming the distal end of the catheter with a flexible, resilient curve and by providing a stainless steel control wire within the lumen during insertion. The control wire is held by a control mechanism or manipulator which permits it to be moved axially of the catheter, forwardly into the curve, to within a fraction of an inch of the distal end and rearedly from the curve. When the control wire is in its forward most position, extending past the curve, it causes the curve in the catheter to substantially straighten so that the catheter may be directed forwardly during insertion. When the wire was withdrawn from the catheter tip, its curved shape is resumed and the catheter may be caused to enter a branching vessel. Thus, the wire is often referred to as a "deflector" wire.

The tip of my earlier guidable catheter assembly was formed with a double curvature including a distal curve which functions as desired above, and a few inches proximal thereof a secondary curve, which facilitates the leading of the catheter by riding against the wall opposite the cannulated orifice.

The catheter manipulator consists of a manually operated assembly to which the proximal end of the catheter is connected to communicate with a fluid supply channel formed in the forward portion of the device. This portion preferably included a swivel joint by which the forward end may be rotated independently of the rearward portion to rotate the catheter during insertion.

The rearward portion of the fluid supply channel communicates with one or more fluid inlet fittings, and terminates in a fluid-tight gland through which the control wire passes.

To the rearward of the fluid supply channel is a slide mechanism controlling the fore and aft motion of the stainless steel control wire. This consisted of a slidable member to which the end of the control wire is loosely attached and which is free to slide back and forth axially of the fluid supply channel.

The manipulator is thus provided not only for control of the catheter, both by rotation and fore and aft motion of the control wire, but also for the introduction of appropriate fluids both during the time that the catheter is being inserted and afterwards when an injection is to be made. In addition, the manipulator is designed to be easily disassembled for cleaning.

However, a problem arose in my earlier design causing the control wire to bind within the lumen when the catheter was inserted into a blood vessel. Obviously, the binding of the control wire within the catheter significantly impairs the physician's ability to properly guide the catheter along its entire course of travel. Binding occurred with axial wire movement. The double curvature of my prior art catheter exacerbated the binding problem.

BRIEF SUMMARY OF THE INVENTION

The subject invention provides a simple and effective catheter and control wire system which is completely guidable within the human body including within a blood stream.

Generally, the subject invention comprises a specialized control wire or deflector wire formed of a stainless steel core covered at least in part with a low friction material and axially slidable within a catheter of the type described above. The deflector wire is resiliently biased into a linear orientation for the purposes of selectively urging the distal curved portion of the catheter into relaxed and unrelaxed positions. In order to discourage the above-mentioned binding effects, the deflector wire of the present invention is covered on its outer surface with a layer of a lubricating or low-friction material. One such preferred material is polytetrafluoroethylene (PTFE) commonly available as Teflon ® (a registered trademark of E. I. Dupont). Other lubricating materials may also be used including hydromers.

In accordance with a further aspect of the invention, there is provided a method of controlling the distal curved portion of a catheter by axially positioning a resilient control wire within the catheter on a polytetrafluoroethylene bearing surface. The method includes providing a polytetrafluoroethylene coating on at least a portion of the outer surface of the stainless steel control wire.

BRIEF DESCRIPTION OF THE DRAWINGS

A preferred embodiment of the invention is described in detail below with reference to the accompanying drawings in which:

FIG. 1 is a top view showing a catheter manipulator with the catheter and control wire of the present invention attached;

FIG. 2 is a side view of the manual control portion of the catheter manipulator of FIG. 1;

FIG. 3 is a side view of the manipulator portion of FIG. 2 in cross section;

FIG. 4 is a top view of the catheter manipulator of FIG. 1 in cross section;

FIG. 5 is a side view of the control wire removed from the catheter illustrating both proximal and distal ends; and, FIG. 6 is a side view of the control wire within the catheter shown in partial cross section.

DETAILED DESCRIPTION OF THE PREFERRED EMBODIMENTS

As shown in FIG. 1, the catheter 10 is fastened to the forward end of manipulator 12 by a conventional Luer Lok arrangement 14.

The catheter 10 consists of a tubular body portion 16 which is typically about 40 inches long and is preferably made of flexible plastic material with an intermediate braided wire sheath which provides a soft flexible construction having torsional rigidity. The tip 18 of the catheter is formed of unreinforced soft plastic material of the type conventionally used and includes a distal curved portion A and about 2 inches proximal thereof a secondary curved portion B. The distal curve A serves the purpose of directing the catheter during its insertion into a desired branching vessel, depending on the rotation of the catheter and on the extent to which the distal curve is caused to be straightened as will be explained below. The secondary curved portion B is provided to assure of there always beings some curvature to the catheter so that it will ride along and be guided by the wall of the vessel opposite the incision through which it is introduced and opposite the entry of any branching vessel into which it is guided.

A control wire 20 within the catheter is arranged for reciprocal motion within the distal curved portion, which when advanced, will cause the distal curve to straighten substantially. The control wire 20 includes a stainless steel core covered with an outer layer of lubricating material such as polytetrafluoroethylene (PTFE). The preferred embodiment uses a low friction material commonly available as Teflon ®.

The control wire runs the entire length of the catheter and extends outwardly from its fitting into the manipulator 12. The manipulator includes a forward fluid supply channel portion 22 which connects to one or more inlet fittings 24, and a rearward wire control slide mechanism 26 which is axially aligned with the fluid supply channel and with the end of the catheter 10.

The fluid supply channel portion of the manipulator includes two rotatably interconnected centrally bored members 28 and 30 as best seen in FIGS. 3 and 4. The rearward one, 28, terminates at its forward end in an elongated snout 32, which is rotatably received in a bore 34 formed in the rearward end of the forward rotatable member 30. The bore 34 is partly surrounded by a neck 36 which terminates in an outwardly extending radial flange 38 by which the forward member 30 is held in place by an inwardly flanged sleeve 40 threaded to the forward end of the rearward rotatable member 28.

A fluid tight rotatable joint between the snout 32 and bore 34 of the fluid supply channel is provided by an O ring 41, at the forward end of the neck 32, retained in a groove 42, and a high pressure seal 43 sealing the base of the neck 32. The O ring 41 is compressed radially between the neck 32 and the bore 34 while the high pressure seal 43 is compressed axially between the base of the neck 34 and the flange 38.

The forward end of the forward member 30 terminates in a standard Luer Lok arrangement 14, and the body of the forward member 30 is enlarged and knurled so that it may be easily grasped by the fingers for rotating it. The tubular body portion 16 of the catheter 10 rotates with the Teflon ® coated stainless steel control wire 20 as the member 30 is manually rotatably advanced.

The rearward end of the fluid supply channel is closed by the high pressure seal 43. No blood or other bodily fluids flow beyond this point. A guide block 48 is formed with a forward central bore 50 axially aligned with the channel 22. To the rear of the bore 50 is a guide groove 52 which opens into a longitudinal slot 54 shown in FIG. 1. The wire 20 is held by the slide mechanism 26 which is constructed with a tubular forward portion 57 which rides in the bore 50 and an enlarged rearward portion 58 which rides in the guide groove 52. An opening 59 extends through the length of the slide mechanism 26 and terminates in an enlarged cup which is closed by a cap 63, and the Teflon ®-coated control wire 20 extends through the bore 59 and ends in a bead 62 which is retained in the cup 60 and provides a connection by which the wire may be moved in either direction.

A thumb control extension 64 connects from the enlarged rearward part 58 of the slide mechanism 26 through the slot 54 to a control knob 66 which is positioned toward the forward end of the guide block for easy access to the thumb.

With particular references now to FIGS. 5 and 6, the control wire 20 is formed of a stainless steel core 70 coated with a low friction and blood impervious material 72. In the preferred embodiment, the core 70 is between 0.020 inches and 0.025 inches in diameter. The low friction material best suited for interfacing the stainless steel core 70 of the control wire with the catheter passage has been found to be Teflon ®, a popular polytetrafluoroethylene P.T.F.E. material available from the E. I. Dupont Company.

The distal end 74 of the control wire 20 includes a small ball portion 76 (FIG. 1) approximately 0.032 inches in outer diameter. The ball portion 76 is smooth and slightly larger in diameter than the core 70 to promote axial travel within the catheter without binding such as would occur would the end 74 be terminated abruptly leaving a sharp circumferential edge.

In the preferred embodiment, the entire outer surface of the control wire 20 is coated with the low-friction polytetrafluoroethylene, from the tip 74 to the bead 62. However, to save costs, only those portions of the coated wire 20 between the seal 43 and the end 74 need be covered since ideally blood does not migrate beyond the seal member as indicated above.

From the foregoing it will be seen that the fluid supply channel portion of the manipulator includes a rotatable joint which includes the enlarged and knurled body portion of the forward member 30 which may be readily grasped for turning. At the same time the thumb control knob 66 for the guide wire may be moved forward and back to cause the Teflon-coated guide wire to extend into or retract from the distal tip of the catheter and thereby control its curvature.

In use, the catheter 10 is introduced into the blood vessel in the usual way, such as through use of my hemostasis cannula described in U.S. Pat. No. 4,000,739, the teachings of which are incorporated herein by reference. After the hemostasis cannula has been positioned within the vessel, the control wire 20 which has been mounted in the manipulator 12 is inserted into the catheter lumen, and the manipulator Luer Lok 14 fitting is attached to the catheter fitting. Appropriate fluid supplies are connected to the manipulator, e.g., to introduce heparinized saline during insertion, and the catheter, under the control of the manipulator, is pushed through the hemostasis cannula and into the blood vessel. Opaque media can be inserted at any time during the insertion or positioning of the catheter to determine the general condition of the aorta and its branching vessels. This is not possible where a guide wire alone is used. Guiding the catheter is accomplished by twisting the forward portion 30 of the fluid supply channel 22, to turn the tip 18 from side to side and by moving the central knob 66 forward and aft to control the curvature of the distal tip portion A, in each case, the outer surface of the control wire interfacing the inner surface of the tubular body portion 16 on a low-friction bearing surface material such as PTFE.

After use the manipulator may be completely disassembled by lifting the knob 66, removing the slide mechanism 26, and withdrawing the wire, unscrewing the Luer Lok 14 to disconnect the catheter, unscrewing the collar 40 to separate the forward and rear portions 28 and 30 of the fluid supply channel 22, and unscrewing the guide block 48 to remove the high pressure seal 43. When thus disassembled, the several parts are easily cleaned by conventional techniques.

Although this invention may be used with conventional catheters having curved tips, I prefer a tip formed of smooth soft thermoplastic material, e.g., elastomeric polyurethane such as Estane which is described in Modem Plastics Encyclopedia for 1965, at page 170. The preferred tip is about three inches long, and heat set to form the many different curves used in catheterization. Also, I prefer Teflon ® material as providing the low-friction bearing surfaces because of its "inertness" with respect to blood.

Further, while the preferred embodiment of the instant invention can be used with conventional catheters as described above, the invention includes all control wires including a lubricated surface and particularly sized according to the length of the catheter and diameter of the lumen. That is, the invention includes a control wire having a length suitably matched with that of the length of the catheter in order to preclude the wire from protruding beyond the catheter tip. The invention also includes a control wire sized according to the length of the catheter so as not to be too short to straighten the biased or resiliently curved tip of the catheter.

Having thus described the invention, I now claim:

1. A catheter apparatus for use with an operatively associated manipulator assembly of the type having an axially slidable member manually operable to cause a change in the curvature of the catheter, the catheter apparatus comprising:
   an elongate non-metallic tubular body member having a flexible curved distal tip portion the tubular body member defining a lumen of the catheter;
   an elongate control wire in the lumen of the catheter and extending substantially the full length of the catheter into said distal tip portion, said control wire being freely slidable within said lumen and connected to the slidable member of the operatively associated manipulator assembly effect motion control over said flexible curved distal tip portion responsive to a position of the slidable member; and,
   a coating on at least a portion of said control wire for providing a low friction surface interface between the control wire and the lumen of the catheter.

2. The catheter apparatus according to claim 1 wherein said coating of the control wire comprises a PTFE material.

3. The catheter apparatus according to claim 1 wherein said coating of the control wire covers substantially the entire outer surface of the elongate control wire.

4. The catheter apparatus according to claim 1 wherein said elongate control wire includes a substantially spherical tip adapted to slidably engage said lumen.

5. The catheter apparatus according to claim 1 wherein said coating comprises a blood impervious material.

6. A catheter apparatus for use with an operatively associated manipulator assembly of the type having an axially slidable member manually operable to cause a change in the curvature of the catheter, the catheter apparatus comprising:
   an elongate non-metallic tubular body member having a flexible curved distal tip portion the tubular body member defining a lumen of the catheter;
   a control wire in the lumen of the catheter running substantially the full length of the catheter into said distal tip portion, said control wire being freely slidable within said lumen and connected to the slidable member of the operatively associated manipulator assembly by a bead, to effect motion control over said flexible curved distal tip portion responsive to a position of the slidable member;
   a distal ball tip formed on the distal end of said control wire; and,
   a bearing surface coating on at least a portion of said control wire for providing a low friction surface interface between the control wire and the lumen of the catheter.

7. The catheter apparatus according to claim 6 wherein said coating of the control wire comprises a PTFE material.

8. The catheter apparatus according to claim 7 wherein said coating of the control wire covers substantially the entire outer surface of the control wire and the distal ball tip portion.

9. The catheter apparatus according to claim 6 wherein said coating comprises a blood impervious material.

10. The catheter apparatus according to claim 6 wherein said control wire includes a core portion covered by said coating and having a diameter of 0.025" or less.

11. The catheter apparatus according to claim 6 wherein said distal ball tip defines a sphere having a diameter of about 0.032".

12. The catheter apparatus according to claim 7 wherein said coating covers substantially the entire outer surface of the control wire and the distal ball tip.

13. A method of using a curved catheter apparatus with an operatively associated manipulator assembly of the type having an axially slidable member manually operable to cause a change in the curvature of the catheter and a rotatable member manually rotationally operable to cause a rotation of the catheter, the method comprising the steps of:
   providing a non-metallic catheter having a flexible curved distal tip portion;

providing a control wire in the lumen of the catheter running substantially the full length of the catheter into said curved distal tip portion, said control wire being freely slidable within said lumen and connected to the slidable member of the operatively associated manipulator assembly to effect motion control over said flexible curved distal tip portion responsive to a position of said manipulation assembly, the control wire being coated on at least a portion thereof with a first material providing a low friction surface interface between the control wire and the lumen of the catheter; and, manipulating the slidable member of the operatively associated manipulator assembly to urge the control wire connected thereto into axial motion within the lumen of said catheter on said low friction surface interface.

14. The method of using a catheter apparatus according to claim 13 further including the step of manipulating the rotatable member of the operatively associated manipulator assembly to urge the tip of the catheter into motion relative to said control wire on said low friction surface interface.

15. The method using a catheter apparatus according to claim 13 wherein:

said control wire providing step includes providing a distal tip ball portion on an end of said control wire; and, said manipulating step includes urging the control wire and distal tip ball portion into axial motion within the lumen of the catheter.

16. An apparatus comprising in combination:
a catheter including:

an elongate non-metallic flexible tubular body member defining a lumen and having a curved distal tip portion;

an elongate substantially inflexible control wire in the lumen of the catheter running substantially the full length of the catheter into said distal tip portion, said control wire being freely slidable within said lumen; and, a coating on at least a portion of said control wire for providing a low friction surface interface between the control wire and the lumen of the catheter; and, a manipulator assembly including:

an axially slidable member connected to the control wire, the slidable member being manually operable to cause axial motion of the control wire within the lumen selectively urging the curved distal tip portion into relaxed curved and unrelaxed elongate positions alternatively.

17. The combination according to claim 16 wherein said coating comprises a PTFE material.

18. The combination according to claim 16 wherein said coating comprises a blood impervious material.

19. The combination according to claim 16 wherein said control wire includes a core portion covered by said coating and having a diameter within the range of 0.020"–0.025".

20. The combination according to claim 19 wherein said coating covers substantially the entire outer surface of the elongate control wire.

21. The combination according to claim 16 wherein said elongate control wire includes on a distal end thereof a substantially spherical tip adapted to slidably engage said lumen.

22. The combination according to claim 21 wherein said spherical tip defines a ball having a diameter of about 0.032".

* * * * *